(12) United States Patent
Nandigala et al.

(10) Patent No.: US 10,933,196 B2
(45) Date of Patent: Mar. 2, 2021

(54) SYRINGES WITH IMPROVED LOCKING UNITS

(71) Applicants: Virchow Biotech Pvt. Ltd, Hyderabad (IN); Virchow Biotech Inc., Arlington, VA (US)

(72) Inventors: Hemanth Nandigala, Hyderabad (IN); Murali Krishna Reddy Tummuru, Hyderabad (IN); Prasad Vure, Secunderabad (IN)

(73) Assignees: Virchow Biotech Pvt. Ltd., Hyderabad (IN); Virchow Biotech Inc., Arlington, VA (US)

( * ) Notice: Subject to any disclaimer, the term of this patent is extended or adjusted under 35 U.S.C. 154(b) by 443 days.

(21) Appl. No.: 15/667,355

(22) Filed: Aug. 2, 2017

(65) Prior Publication Data

US 2018/0043103 A1 Feb. 15, 2018

(30) Foreign Application Priority Data

Aug. 10, 2016 (IN) .............................. 201641027376

(51) Int. Cl.
*A61M 5/315* (2006.01)
*A61M 5/20* (2006.01)

(52) U.S. Cl.
CPC .... *A61M 5/31541* (2013.01); *A61M 5/31501* (2013.01); *A61M 5/31565* (2013.01); *A61M 2005/2073* (2013.01)

(58) Field of Classification Search
CPC .......... A61M 5/00; A61M 3/00; A61M 5/178; A61M 5/31; A61M 5/20; A61M 5/315; A61M 5/31525; A61M 5/31533; A61M 5/31535; A61M 5/31545; A61M 5/31548; A61M 5/31563; A61M 2005/2073; A61M 5/31501; A61M 5/31541; A61M 5/31565
USPC ....................................................... 604/211
See application file for complete search history.

(56) References Cited

U.S. PATENT DOCUMENTS

| | | | |
|---|---|---|---|
| 4,518,387 A * | 5/1985 | Murphy ................ | A61M 5/422 604/115 |
| 7,329,241 B2 | 2/2008 | Horvath | |
| 2010/0305515 A1 | 12/2010 | Subramanian | |
| 2016/0022920 A1* | 1/2016 | Reeves ............. | A61M 5/31536 604/506 |

* cited by examiner

*Primary Examiner* — Jason E Flick

(74) *Attorney, Agent, or Firm* — Fitch, Even, Tabin & Flannery LLP

(57) ABSTRACT

The present invention relates to a rectal delivery device in the form of a syringe with improved locking mechanism for the delivery of an appropriate dosage of a medicament, thereby minimizing errors. More particularly, the present invention provides syringes with improved lock control units for delivering diazepam formulations for the treatment of patients experiencing epileptic seizures.

15 Claims, 6 Drawing Sheets

SYRINGES WITH IMPROVED LOCKING UNITS

CROSS-REFERENCE TO RELATED APPLICATIONS

This application claims priority to Indian Provisional Application No. 201641027376, filed on Aug. 10, which is incorporated herein in its entirety by reference.

FIELD OF THE INVENTION

The present invention relates to drug delivery systems in the form of syringes with an improved locking and dose setting mechanism for the delivery of an agent, such as a medicament or nutritional supplements, to human or veterinary patients in need thereof. More particularly, the present invention relates to rectal drug delivery syringes with improved locking units so as to ensure the delivery of desired dose of the agent.

BACKGROUND OF INVENTION

Drugs for administration by a syringe are often required to be administered to patients at home by a health care provider. However, different amounts of a drug must be administered by a syringe to different patients, which may depend on a number of factors such as size and weight of the patient, age of the patient, whether the patient is a child or an adult, sex of the patient, etc.

For administration of a proper and desired dose to the patient, the drug delivery devices typically require that the device is manufactured such that the entire volume is metered to deliver the desired dose of the drug, or be convenient for a health care provider at home to easily adjust the volume to be delivered. However, both of these options have certain drawbacks.

In the first case, the manufacturer is required to make several versions of a device, with each version including a different volume (usually incremental) of the drug. Further, because several different versions of the device are required, both the distributor of the drug and the pharmacist are required to use more "shelf space" by keeping an inventory of the various devices containing different amounts of the drug.

In the second case where the dose is required to be adjusted at home, it is more likely that the health care provider might make an error in setting the proper dosage. This could be especially important if the patient requires an immediate injection of the drug (due to a medical emergency).

Thus there remains a need for a delivery system that can be adjusted at a suitable dispensing location such as at a pharmacy or a nursing station or at home, such that said system employs a conventional syringe for delivering an adjustable pre-set dosage of a drug.

U.S. Pat. No. 7,329,241, describes an adjustable dose rectal drug delivery device that administers a pre-set dose of a drug such as diazepam for the treatment of patients experiencing epileptic seizures.

U.S. patent application Ser. No. 12/789,373, now abandoned discloses a syringe directed to address the shortcomings of a conventional syringe. This syringe, if not properly used by the healthcare provider in setting the dose, fails to achieve all of the desired benefits. The pharmacist needs to align colors on a ring dial on the plunger and on the syringe barrel and then lock the ring dial at the proper location. If the ring dial is not properly and fully locked, an error can result in the amount of medication delivered to the patient. This can be harmful to patients.

Another U.S. patent application, publication no. 2016/0022920, describes syringes with locking assembly, designed so as to minimize errors in the delivery of medicament. However, the drawback associated with this syringe is that they are supplied in plurality of packs with plurality of different lock units for each syringe, resulting in increased manufacturing and packaging cost. The pharmacist or distributor also needs to increase the shelf-space for maintaining an inventory of various syringe packs with different sized lock units.

There also remains a continuous need for a drug delivery system for the treatment of patients experiencing epileptic seizures. Typically, patients who suffer increased and intermittent seizure activity due to epilepsy are treated via a rectal drug delivery device that administers a pre-set dose of a drug such as diazepam in a gel form. As discussed above, however, there is a need for a system that employs a simplified, economical and user-friendly syringe for delivering an adjustable pre-set dosage of a drug.

OBJECT OF THE INVENTION

Therefore, in one aspect the present inventors intend to develop a rectal drug delivery system in the form of a syringe with improved locking mechanism, which would be convenient to administer and reduce the possibility of errors by pharmacist or a healthcare provider or others in setting the desired dose to be dispensed by the syringe.

An object of the invention is to provide a drug delivery system having an improved locking system so that the desired dosage can be set by a pharmacist or a health care provider, thereby decreasing the risk of dispensing an undesired dosage. More particularly, it is an object of the invention to provide a syringe with an improved lock control mechanism for rectal drug delivery.

It is an object of the invention to provide for a device having an adjustable mechanism for determining dosage so that a dispenser or other provider is not obligated to stock several delivery devices having different dosages.

It is also an object of the invention to make the delivery of a proper amount of a medication essentially foolproof.

A further object is to provide a device and a method for reducing the possibility of errors in dispensing by a pharmacist or a healthcare provider in setting the dose to be dispensed by a syringe of the present invention.

It is also an object of the invention to provide a rectal drug delivery syringe which is simplified, economical and user-friendly, thereby overcoming the drawbacks of the prior art devices.

Also it is an object to provide a method for dispensing the desired amount of drug using the device of the present invention.

Yet another object of the invention is to provide a syringe type device with an improved locking system for the delivery of a desired amount of a drug suitable for patients in need of rectal route of administration.

SUMMARY OF THE INVENTION

In accordance with an aspect of the present invention, the present invention is drawn to a drug delivery device with an improved locking mechanism for dispensing a desired dosage of the medicament.

In preferred embodiments, the present invention provides a syringe with improved lock control units for rectal drug delivery.

In an embodiment, the present invention provides a syringe type drug delivery device with improved lock control units and a dose setting check nut which meets the objectives set forth above.

In some embodiments, a syringe is provided with a locking mechanism, wherein a locking nut is positioned between the body of the syringe comprising a cartridge and the end of the plunger affixed to a piston.

In some embodiments a syringe is provided with a provision for a lens for determining if the dose setting mechanism has been properly set for the desired dosage of medication to be delivered to a patient.

In some embodiments, the present invention provides a syringe comprising a syringe body housing a glass cartridge of about 3 mL capacity, wherein the tip of the syringe is sealed with a plug, followed by a safety cap at its distal end.

In another embodiment, the present invention provides a device in the form of a syringe having an improved locking mechanism, wherein a cylindrical shaped lock nut is positioned at the lower end of the syringe. The lock nut is so configured to engage itself against a circular flange at the lower end of the syringe body.

In yet another embodiment, the present invention provides a syringe with a plunger assembly passing through the locking nut at the proximal end. The plunger assembly comprises a plunger shaft attached to a piston at one end and a dose setting check nut affixed on the other end of the shaft. The piston comprises a structure to conform to the receiving surface of the lock nut.

In a further embodiment of the invention, the syringe comprises a dose setting check nut affixed on the saw toothed design of the plunger shaft. The check nut is positioned on the plunger by means of a clip and the desired amount of a dose may be set by turning the check nut on the desired marks graduated on the plunger. The check nut is also provided with a lens which acts as a dose displaying window to confirm the adjusted dosage.

The present invention also discloses a method of delivery of the drug by the device of the present invention.

In another embodiment, the present invention provides a rectal delivery syringe with improved lock control and dose setting mechanism for the treatment of patients experiencing epileptic seizures.

BRIEF DESCRIPTION OF THE DRAWINGS

The above benefits and various advantages of the several embodiments of the present invention will be more apparent from the following detailed description along with exemplary embodiments a list of the accompanying drawing figures is as below.

DETAILED DESCRIPTION OF THE INVENTION

Figure 1:
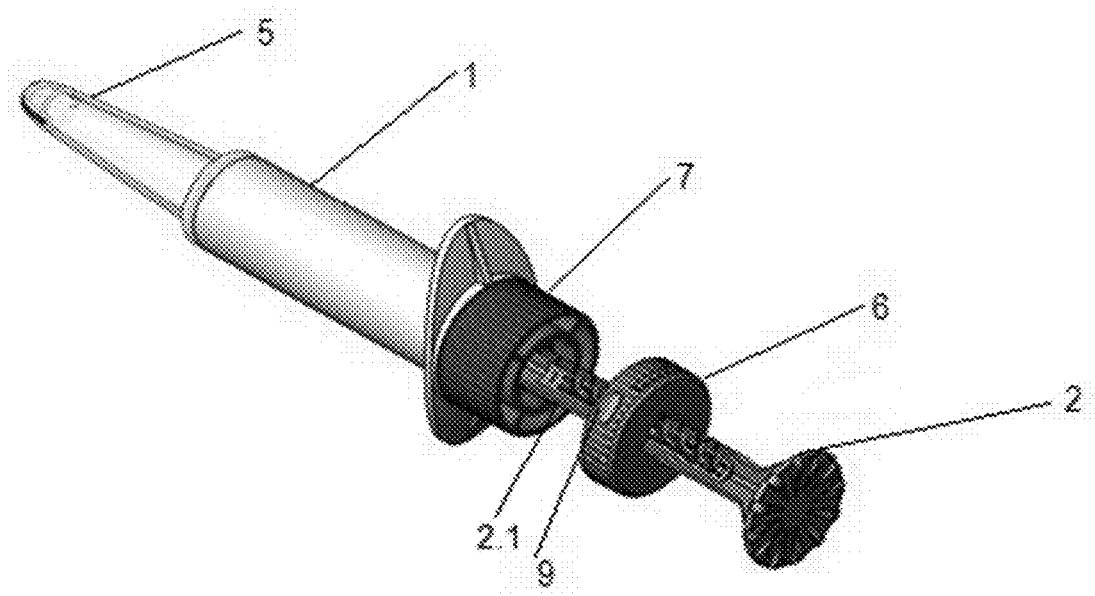
FIG. 1 shows one assembled drug delivery syringe according to an embodiment of the present invention.

The present invention is directed to a rectal drug delivery device in the form of a syringe with an improved locking mechanism to preclude errors while dispensing a predetermined dosage of a drug.

The present invention is drawn to a method of delivery of an agent, medicament or nutritional supplements to human or veterinary patients, using the device of the invention.

Unless otherwise indicated, all technical and scientific terms used herein have the same meaning as commonly understood by one having ordinary skill in the art to which the invention belongs.

The terms "drug," "agent," "medicament," as used herein refer to any substance which shows a physiological effect when ingested or otherwise introduced into the body, and are used interchangeably for the purpose of the invention.

The term "dosage" as used herein refers to a drug or a medicament to be administered to a patient in prescribed amounts at prescribed intervals.

The terms "formulation" and "drug formulation" as used herein means a product comprising a drug or an agent or a medicament, together with pharmaceutically acceptable excipients, said formulation being useful for treating, preventing or reducing the severity of a disease or disorder by administration of said formulation to a subject in need thereof, and are used interchangeably for the purpose of the invention.

The term "treatment" as used herein is defined as the management and care of a patient, e.g. a mammal, in particular a human, for the purpose of combating a disease, condition, or disorder.

The term "patient" as used herein refers to an animal, preferably a mammal, including a human or non-human. The terms patient and subject may be used interchangeably.

The term "cartridge" as used herein refers to a device for facilitating the storage and delivery of pharmaceutical formulations.

The terms "locking nut" and "locking unit" are used interchangeably for the purpose of the invention.

The drug delivery system of the present invention may be described to comprise a syringe with an improved locking mechanism, wherein a lock nut is positioned between the body of the syringe comprising a cartridge and the end of the plunger affixed to a piston. The lock nut attaches to the lower end of the syringe body. The locking system preferably wraps around the shaft of the plunger passing through the unit.

In one embodiment of the invention, the syringe comprises a cylindrical body made of Poly propylene, adapted for housing a multiple dose cartridge containing the medicament. In preferred embodiments of the invention, the cartridge is made of glass or COP (Cyclic olefin polymer) or COC (Cyclic olefin copolymer), preferably glass. The body of the syringe is so designed to receive a cartridge plug at its distal end protected by a safety cap, and further comprises a hand contact part at the proximal end. The plug for the glass cartridge is made of Acrylnitril Butadien Styrol (ABS) or Polycarbonate (PC), and preferably Polycarbonate. The plug acts as a seal for the glass cartridge at the distal end, which is replaced during operation. A safety cap made of polypropylene or polyethylene or low density polyethylene is provided, which acts as a safety cover to the cartridge plug when the device is not in use. The safety cap is designed such that it can be easily removed during use by a flip of a thumb. The hand contact part of the syringe body facilitates easy handling of the device by the dispenser during operation. The syringe body housing the cartridge is provided with a circular flange at its lower end for attaching itself to a locking nut. The syringe body is adapted to slidably receive the plunger through it. However, the locking nut limits or controls or restricts the travel of the plunger and thus the amount of medication that can be delivered by the syringe. The syringe body surrounds a portion of the plunger during operation and contains the medicament or the substance to be delivered.

In another embodiment, the syringe of the invention has a plunger assembly comprising a rubber piston at one end, a shaft attached to the piston, and a dose setting check nut at the other end. The plunger is made up of Acrylnitril Butadien Styrol (ABS) or Polycarbonate (PC) and preferably Polycarbonate has a saw tooth like design, which is calibrated with dosage strengths grooved on it. The plunger in some embodiments comprises a central core and four flanges that run through the length of the plunger. Two of the flanges have straight edges and the remaining two flanges have toothed edges. The flanges with straight edges are graduated with dosage markings and the flanges with toothed edges correspond to the dosage markings on the flanges with straight edges.

The plunger may be fixed with a check nut which acts as dial ring for setting the desired dosage marked on the plunger. In preferred embodiments of the invention, the check nut is made of Acrylnitril Butadien Styrol (ABS) or Polycarbonate (PC) and preferably Polycarbonate. The check nut may be positioned on the plunger by means of a clip made of PC, and locked on the toothed projections of the plunger, adjusted at the desired dosage mark resulting in the syringe delivering an accurate dose. The check nut also has a lens made of PMMA or Plexiglas, embedded on it which helps the pharmacist or health care provider in determining if the dose setting mechanism has been properly set for the desired dosage of medication to be delivered to a patient. The syringe when locked at any strength results in the exact desired amount of substance to be delivered.

In one embodiment, the device also comprises an improved lock control system of a single dimension that can be used by pharmacists or others in the preparation of syringes. In some uses of prior art syringes, the syringes are provided to pharmacists in packs with a plurality of syringes which, when filled, provide kits or packets to the user or health care provider which desirably have two or more syringes. In such instances a packet has two syringes and a plurality of different lock units for each syringe. The length or dimension of the lock units is sized to provide a specific dose of an agent. The pharmacist selects and usually uses one appropriate lock unit of the same dimension for each syringe depending on the required dose. The pharmacist then disposes of the unused lock units or returns them to the source of the syringe and unit locks. However, the syringes of the present invention are provided with a single lock control nut of a particular dimension, suitable for delivering any dosage of a medicament thereby reducing the manufacturing cost and increasing the shelf-space in a pharmacy or a nursing station.

In another embodiment, the syringes of the present invention are advantageous in that they reduce the burden on the part of the dispenser or healthcare provider. In some instances, when the user or health care provider receives the prior art locked syringes, that person needs to check the applied lock unit, compare it with the prior used syringes, if available, and be assured that the dose in the present syringe is the same as previously used. This is a system and method of visually double checking the dose that is to be applied. However, this would become strenuous for the dispenser and time consuming, especially when the patient is in urgent need of medication. Thus the syringes of the present invention with an improved lock control unit provide a simple and user friendly handling.

Various embodiments of the invention may be illustrated with reference to FIGS. 1-6.

FIG. 1 shows the assembled drug delivery syringe of the present invention comprising a cylindrical syringe body (1) protected with a safety cap (5). The syringe body (1) has a plunger (2) inserted therein passing through a lock nut (7). The lock nut (7) comprising the lock control unit is positioned between the lower end of the syringe body (1) and the piston end of shaft of the plunger (2). A check nut (6) is positioned on the shaft of the plunger for setting the required dosage of the drug to be administered. The check nut (6) is provided with a lens (9) for a glance by the dispenser to make sure if the desired dosage has been adjusted.

Figure 2:
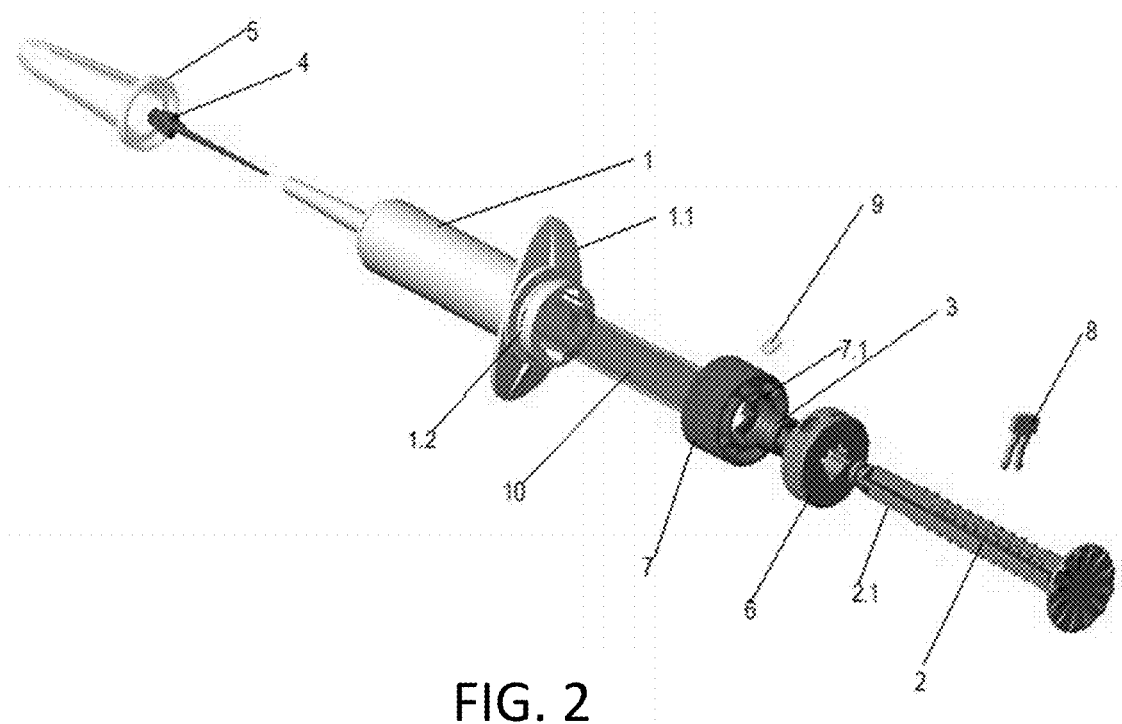
FIG. 2 shows an exploded view of a drug delivery syringe according to one embodiment of the present invention.

FIG. 2 is a demonstration of the exploded view of the drug delivery syringe of the present invention comprising a syringe body (1) housing a cartridge (10) filled with a drug formulation to be dispensed. In an embodiment, the cartridges of the invention are preferably made of glass. After the drug is exhausted, the user may detach the cartridge from the syringe housing and then remove the empty cartridge and replace the empty cartridge with a filled cartridge.

The FIG. 2 shows the syringe (1) with a hand contact part (1.1) at its proximal end for easy handling of the device. The distal end of the syringe (1) receives a plug (4) for glass cartridge (10), sealing the open end of the syringe. The syringe body (1) is configured to receive a safety cap (5) protecting the plug (4), which may be removed during operation and replaced later. A lock nut (7) is positioned at the base of the syringe body (1). In an embodiment of the invention, the lower body of the syringe comprises a circular flange (1.2) for affixing the lock nut (7) in place. The lock nut (7) is cylindrical in shape and has a receiving surface (7.1) with a structure to conform to the shape of the piston (3) from the shaft (2.1). In preferred embodiments, and as illustrated in FIG. 2, the piston (3) has a round projection that fits into the circular receiving groove of the lock unit (7). In some embodiments, other possible geometries and configurations of the lock nut (7) and piston (3) fall within the scope of the invention.

The piston (3) is attached to one end of a shaft (2.1) of a plunger (2). The lock unit (7) limits the travel of the piston (3), thereby affecting the travel of the plunger (2) in the syringe, and thus the amount of an agent, such as a medication, delivered from the syringe. In the FIG. 2, a plunger (2) resembles a saw tooth with dosage strength graduations on it. A check nut (6) may be grooved on to the plunger (2) by means of a clip (8) to enhance the grip. This check nut (6) comprises the dose setting mechanism. In operation, the check nut (6) is positioned and clipped at the desired dosage mark on the plunger (2), resulting in delivery of desired dosage of the medicament.

Figure 3:
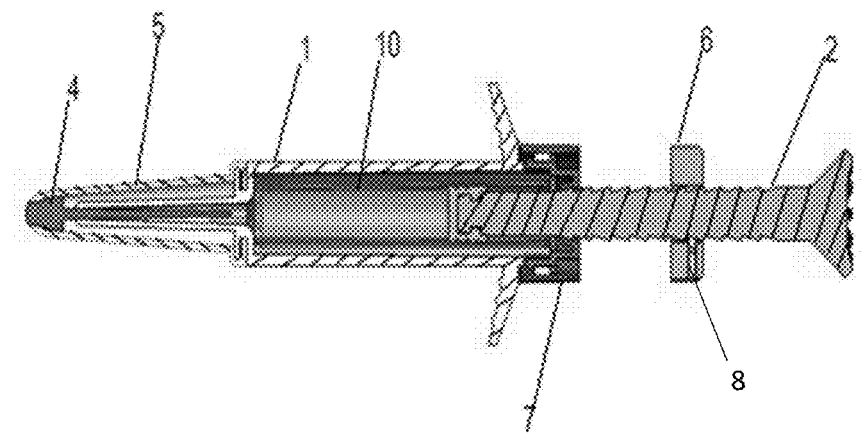
FIG. 3 shows a cross-sectional view of a syringe in accordance with some embodiments of the invention illustrating the locking mechanism.

FIG. 3 is an illustration of a cross sectional view of the syringe with a lock nut (7). As shown in the figure, a glass cartridge (10) is suitably placed in the housing (1) of the syringe. The plunger (2) attached to a piston is slidably disposed within the body of the syringe set to deliver a particular amount of a dosage. The check nut (6) is adjusted on to the plunger (2) at the required dosage mark, responsible for the position of the plunger as shown in the syringe. The lock nut (7) acts a physical barrier, controlling any further movement of the plunger inside the syringe. The lock nut has a receiving surface so that the piston coming from the plunger fits within the surface of the lock nut. This configuration of the lock nut ensures that not more than the prescribed dose is administered and also makes it difficult for the user to pull out the plunger and re-use it.

Figure 4:
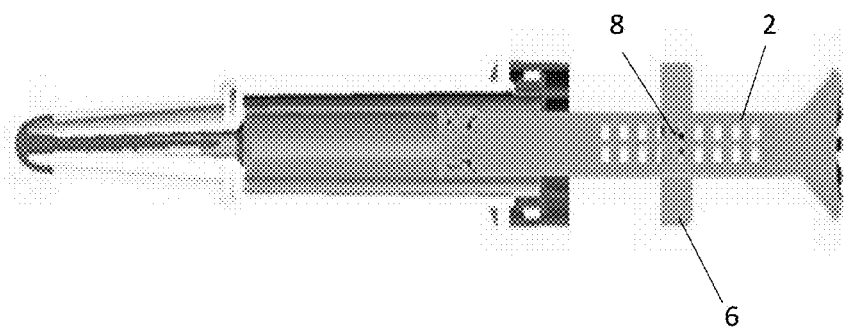
FIG. 4 shows a view of a syringe in accordance with some embodiments of the invention with a cross-sectional illustration of the plunger and dose setting mechanism.

FIG. 4 shows a syringe body with a plunger inserted therein. A cross sectional view of the plunger shows a check nut (6) locked onto the plunger (2) by means of a clip (8). The plunger is calibrated with dosage markings on it flanges, which correspond to different dosages of the medicament to be delivered.

Figure 5:
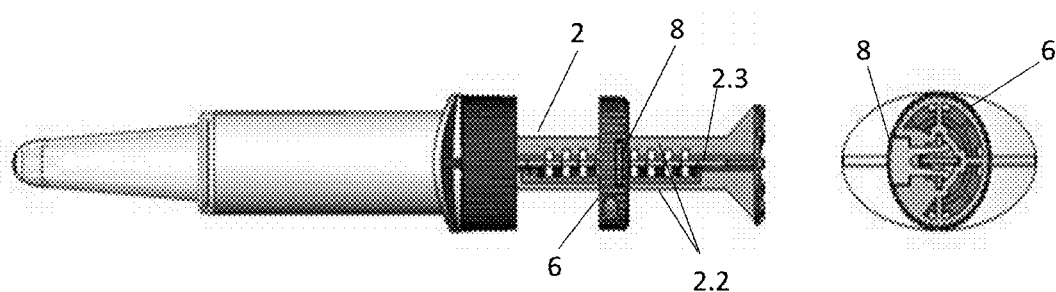
FIG. 5 shows a view of a syringe according to one embodiment of the invention with an illustration of a transverse section of check nut assembly of the device of the invention.
Figure 6:
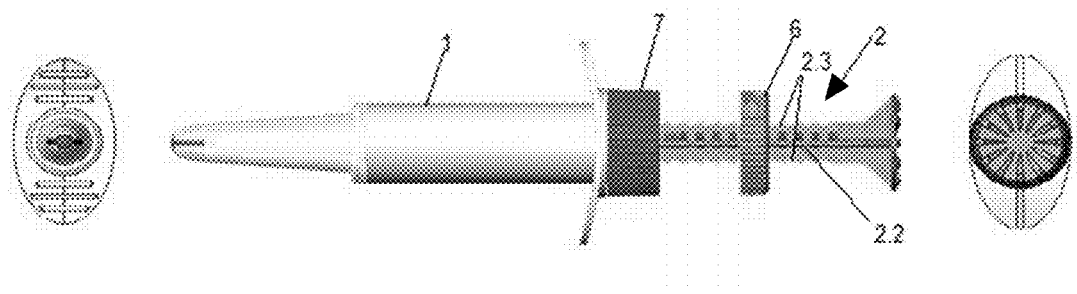
FIG. 6 is an illustration showing multiple side views of the delivery device of the invention.

FIGS. 5 and 6 of the invention illustrates a perspective view of the syringe, wherein the plunger (2) is seen to have a central core and four flanges (only three flanges can be seen in FIG. 6) that run through the length of the plunger. Two of the flanges (2.2) have straight edges and the remaining two flanges (2.3) have toothed edges. The flanges (2.2) are graduated with dosage markings and the flanges (2.3) with toothed edges correspond to the dosage markings on flanges (2.2).

In use, the check nut (6) can fit on the plunger (2) by means of a clip (8) until it is used to set a desired dosage. A particular amount of the dosage can be set by sliding the check nut to the appropriate marking on the plunger flange (2.2) and then twisting the check nut (6) until it engages with the toothed projection on flanges (2.3) of the plunger (2). The check nut comprises a recess of a particular dimension so as to adjust itself on the toothed projections of the plunger. In preferred embodiments of the invention, the check nut may be twisted onto the plunger irreversibly at a particular dosage. FIG. 5 also shows a transverse section through the check nut (6) demonstrating its design and configuration.

FIG. 6 illustrates the front and rear views of the drug delivery syringe of the present invention.

According to an embodiment, the method for delivering a drug using the rectal drug delivery syringe of the present invention comprises, placing a glass cartridge into the syringe housing. During operation, the safety cap is removed easily by a flick of thumb and the cartridge plug is pulled out. The locking nut is then fixed against the circular flange provided at the lower end of the syringe body resulting in a clicking sound. The rubber piston attached to the plunger shaft is then advanced towards the syringe. The dose is set by locking the check nut on to the plunger by means of a clip and adjusting the check nut to a desired dosage on the plunger. The plunger assembly is moved towards the syringe such that it engages with the lock nut. The piston fits into the receiving surface of the locking nut. The desired dose of the drug formulation is administered to the patient by holding the syringe at the hand contact part using one hand, with the other hand holding the patient.

In preferred embodiments of the invention, the syringe comprises a drug formulation for rectal administration. In more preferred embodiments of the invention, the syringe comprises a drug formulation for the treatment of patients experiencing epileptic seizures by rectal administration. In most preferred embodiments, the syringe of the present invention is used to deliver a diazepam rectal gel formulation for the treatment of patients suffering from epileptic seizures.

In other embodiments, the rectal drug delivery device of the present invention is supplied in the form of a kit comprising the syringe, a cartridge comprising the medication, accompanied with an instruction leaflet for administration and disposal of the syringe kit to the dispenser or health care provider. In some embodiments, the syringe kit may optionally be provided with a lubricant for the syringe.

In an embodiment, the rectal drug delivery syringe kits of the present invention have been surprisingly found to yield better results than the prior art syringes. A comparative example 1 shows the results of use of the syringe kit of present invention and the results from the use of kit as disclosed in the U.S. patent application Ser. No. 12/789,373, incorporated herein by reference. The results from the use of the present invention are shown in Table 1.

A comparative example 2 shows the results of use of the syringe kit of the present invention and the results from the use of kit as described in U.S. patent application publication no. 20160022920, incorporated herein by reference.

Comparative Example 1

A study was conducted following U.S. patent application Ser. No. 12/789,373 in which 15 pharmacists were given two kits of Diazepam rectal gel, one in 10 mg strength and one in 20 mg strength, for a total of eight syringes per pharmacist. Four pharmacists in this study failed to lock the syringe. One pharmacist left two syringes unlocked. A second pharmacist left five syringes unlocked, and a third pharmacist left seven syringes unlocked. The result is depicted in Table 1.

TABLE 1

| S. No | Parameter | Success | Success with difficulty | Failures |
|---|---|---|---|---|
| 1 | Locking the Syringe | 11 | 0 | 4 Pharmacists (They left syringes unlocked after the operation) |

The results obtained from the use of kits of the present invention, with 15 pharmacists each given two Diazepam rectal gel kits in 10 mg and 20 mg strengths for a total of eight syringes per pharmacist, is given in Table 3.

Comparative Example 2

A study was conducted following U.S. patent application publication no. 20160022920, wherein 15 pharmacists were provided with two kits of diazepam rectal gel, one in 10 mg and one in 20 mg strength, for a total of eight syringes per pharmacist. The pharmacists were assessed in their ability to select a correct dose collar and locking the same on the plunger. Results showed that six pharmacists failed to select a correct dose collar on ten syringes. Three pharmacists failed to distinguish the color coding of the locking units, which correspond to a common length. Five pharmacists succeeded in locking the collar on the plunger but with a difficulty. One pharmacist left three syringes unlocked. The result is depicted in Table 2.

TABLE 2

| S. No | Parameter | Success | Success with difficulty | Failures |
|---|---|---|---|---|
| 1 | Select Correct Dose Collar | 9 | 0 | 6 Pharmacist |
| 2 | Lock collar on plunger shaft | 0 | 5 | 10 Pharmacist |
| 3 | Locking the Syringe | 14 | 0 | 1 Pharmacist |
| 4 | Distinguish the color coding | 12 | 0 | 3 Pharmacist |

The results obtained from the use of kits of the present invention, with 15 pharmacists each given two Diazepam rectal gel kits in 10 mg and 20 mg strengths for a total of eight syringes per pharmacist, is given in Table 3.

TABLE 3

| S. No | Parameter | Success | Success with difficulty | Failures |
|---|---|---|---|---|
| 1 | Fixing the locking nut | 13 | 0 | 2 pharmacists Two or more locking nuts could not be fixed due to a manufacturing defect |
| 2 | Selecting the right dose | 12 | 2 pharmacists Misreading of the desired dose through lens in one or more syringes | 1 pharmacist Manufacturing defect in one or more check nut |

From the results observed in Table 1-3, it is evident that the syringes of the present invention provide surprisingly better results than the prior art devices. The pharmacist were able to fix the locking nut to the cartridge and set the appropriate dosage more consistently. Thus, the rectal drug delivery syringes of the present invention are found to be superior to the prior art syringes.

Evaluation of Dose Accuracy:

The device of the present invention has been evaluated for Dose Accuracy of the device. Dose Accuracy of the device under test, mainly signifies how less erroneous the dispensed dose is, i.e., the less difference within the intended dose and actual dispensed dose is, the more accurate the pen is.

The Dose Accuracy test was carried out using Water for Injection. The water filled cartridge was inserted within the device. A pharmaceutical balance was used for the assessment of the applied volumes (AX205 Delta Range, Mettler Toledo, Giessen, Germany). Dose of 1 mL was set by the check nut and locknut mechanism. One small 50 mL biker was kept on the balance. Now the dose was delivered by pressing the plunger. The weight was obtained as 0.0012 mg (nearly 1 µg). The same procedure was repeated until the cartridge got empty. The result is tabulated in Table 4.

The same process applied for prior art U.S. patent application Ser. No. 12/789,373 and U.S. patent application publication no. 20160022920 and the results are tabulated in Table 4.

TABLE 4

| Sl. No | Set Dose | Dose Delivered by the device of present invention | Dose delivered by the device depicted in prior art U.S. patent application Ser. No. 12/789,373 | Dose delivered by the device depicted in prior art U.S. patent application publication no. 20160022920 |
|---|---|---|---|---|
| 1 | 1 mL (=0.001 mg) | 0.0011 mg | 0.0008 mg | 0.0007 mg |
| 2 | | 0.0009 mg | 0.00082 mg | 0.0014 mg |
| 3 | | 0.001 mg | 0.0008 mg | 0.0009 mg |

From the above table it is conclude first that the acceptance criteria for dose accuracy is ±10% of intended dose, and secondly that the device represented in the present invention is more accurate than the devices shown in the prior art. Therefore, in terms of dose accuracy the device of present invention is superior to prior art devices.

Without being limited by theory, the device of the present invention may be advantageously used to deliver drug formulations intended for rectal administration, preferably diazepam. The device and the delivery of the drug through the device are such that it prevents the disadvantages of the prior art. It is envisaged that by providing the syringes of the present invention, the delivery of the accurate dosage of a medicament is achieved, thereby contributing to a user friendly handling of the device.

Furthermore, the device of the present invention reduces the economic burden on the part of the manufacturer and also on the pharmacist or a distributor in increasing the shelf-space.

The systems and methods of the present invention may be embodied in other specific forms without departing from the teachings or essential characteristics of the invention.

The foregoing embodiments and advantages are merely exemplary and are not to be construed as limiting the scope of the present invention. The description of the exemplary embodiments of the present invention is intended to be illustrative and not to limit the scope of the invention. Various modifications, alterations and variations, which are apparent to a person skilled in the art, are intended to fall within the scope of the invention.

We claim:

1. A syringe device comprising: a piston, a plunger, a check nut, a cartridge, and a lock nut, wherein the plunger comprises at least a first flange comprising at least one projection and a second flange comprising a flat edge that is slideable within the check nut, and wherein the check nut is rotatable relative to the plunger to engage the check nut to the projection, the plunger further coupled to the piston and locked by the lock nut.

2. A syringe device comprising: a piston, a plunger, a check nut, a lock nut, a plug, and a lens, wherein the plug is for a cartridge and the lock nut and check nut are dimensioned to limit travel of the piston on the plunger to deliver a dose of an agent from the syringe, wherein the plunger comprises at least a first flange comprising at least one projection and a second flange comprising a flat edge that is slideable within the check nut, and wherein the check nut is movable between first orientations and second orientations relative to the plunger and has an interior surface that does not engage the projection in a first orientation and engages the plunger in a second orientation, and wherein the lock nut comprises a first surface, the first surface configured to receive a piston cap and a second surface to receive the cartridge.

3. The syringe device as in claim 1 wherein the check nut comprises a lens.

4. The syringe device in the claim 1, wherein the check nut is rotatable relative to the plunger, and wherein in the first orientation the check nut is slidable relative to the plunger and wherein in the second orientation the interior surface of the check nut engages the projection of the plunger.

5. A plurality of syringe devices of the type of syringes as in claim 1 wherein each of a plurality of lock nuts of differing dimensions from a first surface to a second surface are selectable to limit the travel of the piston and the check nut to dispense different amounts of an agent.

6. The plurality of syringe devices as in claim 5 wherein each of the plurality of syringes is associated with at least two lock nuts, each lock nut having a differing dimension from a first surface to a second surface, whereby selecting and affixing lock nuts of equal dimension for each syringe limits the travel of the piston to the check nut of each syringe to dispense an equal dose of the agent from each syringe.

7. A kit comprising a plurality of syringe devices as in claim 1, the kit further comprising a plurality of lock nuts, wherein lock nuts of one color correspond to a common length and a particular volume of the agent to be controlled by the check nut of one of at least one of the plurality of syringes.

8. The syringe device of claim 1 wherein the cartridge is pre-filled with diazepam rectal gel.

9. The syringe device of claim 1 which is adapted for human, veterinary and agricultural use.

10. A method for limiting a syringe device to provide a specific dose comprising: filling a syringe with an agent, the syringe including: (i) a cartridge; and (ii) a plunger, the plunger is slideable within a check nut when the check nut is in a first orientation relative to the plunger and locked relative to the check nut when the check nut is in a second orientation, , and further locked with a lock nut and wherein the plunger includes a shaft extending from a piston to a plunger cap; selecting the lock nut by a dimension of the lock nut, the selected dimension correlating to a desired dose; affixing the lock nut to the plunger; rotating the check nut to lock the check nut at a desired position along the plunger; limiting travel of the piston in a barrel of the syringe by the affixed lock nut to deliver a dose of the agent from the syringe; and wherein the lock nut comprises a first surface, the first surface includes a recess of a dimension selected to receive a piston cap within the recess.

11. A plurality of syringe devices of the type as in claim 2 wherein each of a plurality of lock nuts of differing dimensions from the first surface to the second surface are selectable to limit the travel of the piston in the check nut to dispense different amounts of an agent.

12. The plurality of syringe devices as in claim 11 wherein each of the plurality of syringes is associated with at least two lock nuts, each lock nut having a differing dimension from the first surface to the second surface, whereby selecting and affixing lock nuts of equal dimension for each syringe limits the travel of the piston to the check nut of each syringe to dispense an equal dose of the agent from each syringe.

13. The syringe device of claim 2 wherein the cartridge is pre-filled with diazepam rectal gel.

14. The syringe device of claim 2 which is adapted for human, veterinary and agricultural use.

15. The method as in claim 10, wherein the check nut is rotatable between a first configuration wherein it is slidable relative to the plunger and a second configuration wherein the internal surface of the check nut engages a toothed surface of the plunger.

* * * * *